US011096899B2

(12) United States Patent
Gong et al.

(10) Patent No.: US 11,096,899 B2
(45) Date of Patent: Aug. 24, 2021

(54) BACTERIAL MEMBRANE NANOPARTICLES AS AN IMMUNOTHERAPY SYSTEM FOR CANCER TREATMENT

(71) Applicant: Wisconsin Alumni Research Foundation, Madison, WI (US)

(72) Inventors: Shaoqin Gong, Madison, WI (US); Zachary Scott Morris, Madison, WI (US); Mingzhou Ye, Madison, WI (US); Ravi Bhasker Patel, Madison, WI (US); Paul M. Sondel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/562,133

(22) Filed: Sep. 5, 2019

(65) Prior Publication Data

US 2020/0078312 A1  Mar. 12, 2020

Related U.S. Application Data

(60) Provisional application No. 62/728,645, filed on Sep. 7, 2018.

(51) Int. Cl.
*A61K 39/39* (2006.01)
*A61K 9/50* (2006.01)
*A61P 35/00* (2006.01)
*A61K 9/51* (2006.01)
*A61K 39/00* (2006.01)

(52) U.S. Cl.
CPC .......... *A61K 9/5068* (2013.01); *A61K 9/5138* (2013.01); *A61K 39/39* (2013.01); *A61P 35/00* (2018.01); *A61K 2039/55561* (2013.01); *A61K 2039/55594* (2013.01)

(58) Field of Classification Search
None
See application file for complete search history.

(56) References Cited

U.S. PATENT DOCUMENTS

2013/0337066 A1* 12/2013 Zhang ............... A61P 31/04
424/489

OTHER PUBLICATIONS

Rice-Ficht et al. 2010 (Polymeric particles in vaccine delivery; Current Opinion in Microbiology; 13:106-112) (Year: 2010).*
Gregory et al. 2013 (Vaccine delivery using nanoparticles; Frontiers in Cellular and Infection Microbiology; 3(13) 1-13). (Year: 2013).*
Gao et al. 2015 (Modulating Antibacterial Immunity via Bacterial Membrane-Coated Nanoparticles; Nano Letters 15: 1403-1409) (Year: 2015).*
Luo et al. 2017 (A STING-activating nanovaccine for cancer immunotherapy; Nature Nanotechnology 12: 648) (Year: 2017).*
Chiaradia et al. 2017 (Dissecting the mycobacterial cell envelope and defining the composition of the native mycomembrane; Scientific Reports 7: 12807) (Year: 2017).*
Tsuji et al; Maturation of Human Denritic Cells by Cell Wall Skeleton of *Mycobacterium bovis* Bacillus Calmette-Guerin: Involvement of Toll-Like Receptors; Dec. 2000; 8 pages.
Latz et al; TLR9 Signals After Translocating from the ER to CpG DNA in the lysosome; Jan. 2004; 9 pages.
Cohn et al.; Dendritic Cell-Targeted Vaccines; May 2014; 11 pages.
Luo et al; A Sting-Activating Nanovaccine for Cancer Imunotherapy; Apr. 2017; 10 pages.
Muller et al; Type I Interferons and Natural Killer Cell Regulation in Cancer; Mar. 2017; 11 pages.
Hadrup et al; Effector CD4 and CD8 T Cells and Their Role in The Tumor Microenvironment; Dec. 2012; 11 pages.
Hamdy et al; Targeting Dentricic Cells with Nano-Particulate PLGA Cancer Vaccine Formulations; Jun. 2011; 13 pages.
Garcia et al; Evaluation of Specific Humoral Immune Response and Cross Reactivity Against *Mycobacterium tuberculosis* Antigens Induced in Mice Immunized with Liposomes Composed of Total Lipids Extracted from *Mycobacterium smegmatis*; Jun. 2011; 5 pages.
Nguyen et al; Evaluation of the Potential of *Mycobacerium smegmatis* as Vaccine Candidate Against Tuberculosis by in silico and in vino studies; Dec. 2009; 7 pages.
Adam et al; Recent Results in Cancer Research; Jun. 1972; 7 pages.
Bansal-Mutalik et al; Mycobacterial Outer Membrane is A Lipid Bilayer and the Inner Membrane is Usually Rich in Diacyl Phosphatidylinositol Dimannosides; Feb. 2014; 6 pages.
Bansal-Mutalik et al; Supporting Information; 6 pages.
Zhu et al; Albumin/Vaccine Nanocomplexes That Assemble in vivo for Combination Cancer Immunotherapy; Dec. 2017; 15 pages.
Min et al; Antigen-Capturing Nanoparticles Improve the Abscopal Effect and Cancer Immunotherapy; Jun. 26, 2017; 8 pages.

* cited by examiner

*Primary Examiner* — Mary Maille Lyons
(74) *Attorney, Agent, or Firm* — Foley & Lardner LLP

(57) ABSTRACT

Provided herein are nanoparticles comprising a polyplex core comprising one or more pH-responsive polymers and one or more anionic immune adjuvants, wherein each pH-responsive polymer comprises ionizable amine groups; and a shell of bacterial cell membrane components at least partially coating the polyplex core, wherein the bacterial cell membrane components comprise TLR 2 and/or TLR 4 agonists. Also provided are methods of stimulating an immune response in a mammal using the nanoparticle.

23 Claims, 15 Drawing Sheets

Specification includes a Sequence Listing.

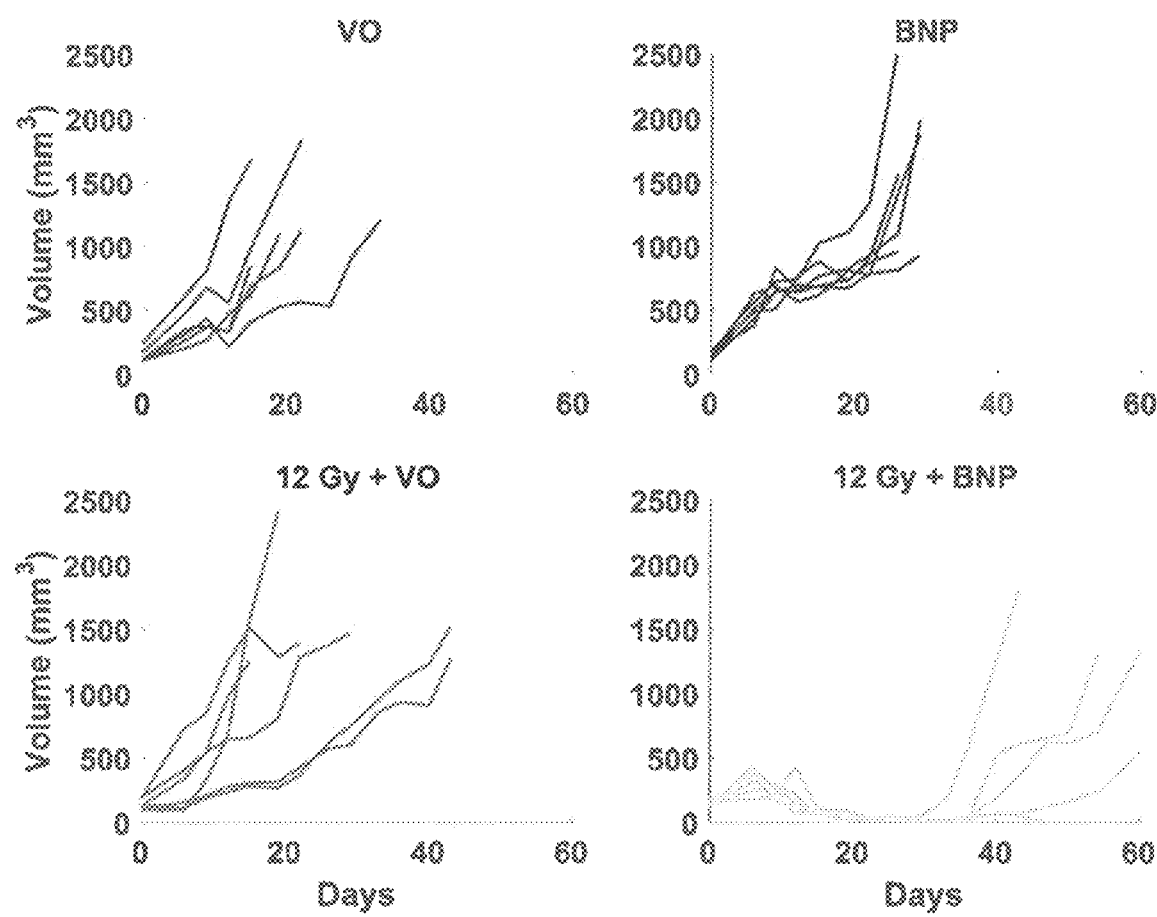

SEQUENCE LISTING

```
<160> NUMBER OF SEQ ID NOS: 60

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acattggctt gcgagacgta                                                      20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```
atcaccttgc caatccccag                                                     20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 3
tttgaatgtg aagttgaccc gt                                                  22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 4
gtgcttgagg tggttgtgga                                                     20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 5
cgactgttgc ctctcgtaca                                                     20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 6
agcttcatcg gccatctgtc                                                     20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 7
acatcatgaa ggtctccacc ac                                                  22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 8
ccatatggcg ctgagaagac t                                         21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctcccactt cctgctgttt                                           20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtctcatagt aatccatcac aaa                                       23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaaggaaccg ccaagtgtgt                                           20

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctagctcat ctccaaatag ttgat                                     25

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgctgcaact gcatccata                                            19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taggctcgca gggatgattt c                                         21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgtgacatcc tgggaacgtc t                                             21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttccaagaca gcagagggtc a                                             21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgctgttctt ttcctcttgg g                                             21

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccttatcact agggttcctc gaa                                           23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gacccccttt cacctatgcc                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggcgaacatg cgagtaaacc                                               20

```
<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtcgagggtt tctctactgg t                                               21

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaaccactgc cagtccacat ag                                              22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgggctttg ctctaccaca                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aagctgcccg ttctcaatca                                                 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gaacaaaaga cgaggcgaag                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccttcctct gctctgacac                                                 20
```

```
<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tccaccagca gacagtgttt c                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcaagtggag agcagttgag g                                              21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcatggccca gaaatcaagg                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gagaaatcga tgacagcgcc                                                20

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgtcaaagat gtccaacttc acc                                            23

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tcttcccgtt gcttgacgtt                                                20

<210> SEQ ID NO 33
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgattcaagg ggacattagg ca                                              22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
accaattcat cccccacacg                                                 20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctctgcaaga gacttccatc ca                                              22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aagtagggaa ggccgtggtt                                                 20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tggtagacag ggtagaagcc a                                               21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tgagacagct ggcaccttga                                                 20

<210> SEQ ID NO 39
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
accacggagt ccaattaccc                                                    20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
actccttggc aggttttgct a                                                  21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agaagtgggc atctgtggtg                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gacaaccaga acagcaacgg                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cggccctgta ttgacctcat                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
actccagaca gtgcttccag                                                    20

<210> SEQ ID NO 45
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 45
gacctgtatc agacacctct                                               20

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
ctgtcgtgtc cttctttgg                                                19

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
taagaggctg ctccgatggt                                               20

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
gacgtcaagg tatgcatctt ggt                                           23

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
tttctcagtc aaaggcgtcc a                                             21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tctatccagt gttctccgtc tg                                            22

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccagccactt ctgagcatga                                                  20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cttctcttcc cactcacggg                                                  20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctattgcttc agctccacag                                                  20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gacagaagtt ggcatggtag                                                  20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gatcccgaaa gtgcgaactc                                                  20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
taccggaacc agcaacttct                                                  20

<210> SEQ ID NO 57
<211> LENGTH: 21
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 57
ttctgcaaag ggagagtggt c                                              21

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgaaggtagg aaggcctgag at                                             22

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aacactctta cctgtgcgct                                                20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcagggaatg agtagacctc ca                                             22
```

US 11,096,899 B2

BACTERIAL MEMBRANE NANOPARTICLES AS AN IMMUNOTHERAPY SYSTEM FOR CANCER TREATMENT

CROSS REFERENCE TO RELATED APPLICATION

This application claims the benefit of and priority to U.S. Provisional Patent Application No. 62/728,645, filed on Sep. 7, 2018, the entire contents of which is incorporated herein by reference in its entirety.

GOVERNMENT RIGHTS

This invention was made with government support under CA166178 and CA014520 awarded by the National Institutes of Health. The government has certain rights in the invention.

FIELD

The present technology relates generally to immunotherapy systems and methods for treating cancer. The compositions of such systems include a polyplex core including pH-responsive polymers and anionic adjuvants. The polyplex core is at least partially coated with bacterial membrane components.

SUMMARY OF THE INVENTION

The present technology provides a nanoparticle (also referred to herein as a bacterial membrane-coated nanoparticle or BNP) that may act as a versatile adjuvant to radiation that can strengthen the multistep cancer immunity cascade and enhance both innate and adaptive immune responses. The nanoparticle includes a polyplex core comprising one or more pH-responsive polymers and one or more anionic immune adjuvants, wherein each pH-responsive polymer comprises ionizable amine groups. The nanoparticles further include a shell of bacterial cell membrane components at least partially coating the polyplex core, wherein the bacterial cell membrane components comprise TLR 2 and/or TLR 4 agonists. Optionally, the nanoparticles include antigen capture groups, e.g., maleimide, on the outer surface of the nanoparticle (shell).

The present nanoparticles may be used generally for cancer immunotherapy. In one aspect the present technology provides a method of stimulating an immune response in a mammal that includes administering an effective amount of a nanoparticle of any embodiment described herein to an irradiated tumor in the mammal, wherein the radiation was an amount effective to release cancer antigens from the tumor and stimulate the immune response. As a result of the immune response, growth of the tumor may be inhibited or the tumor may shrink.

While not wishing to be bound by theory, FIGS. 1A and 1B show an illustrative embodiment of a method of use of the present nanoparticles in which antigen capture groups are present on the surface of the nanoparticles. In this embodiment, BNP is intratumorally injected following radiation therapy (RT) treatment (FIG. 1A). The BNP captures exposed cancer necantigens through antigen capture groups such as maleimide groups. The BNP undergoes highly efficient uptake in antigen-presenting cell (APC) and stimulates immune response due to the presence of its bacterial membrane component shell. The TLR2 and TLR4 agonists among the bacterial membrane components help stimulate the innate immune response and the eventual development of the adaptive immune response. Once the BNP is endocytosed (FIG. 1B), the anionic immune adjuvant is released from the polyplex core and is believed to activate toll-like receptor 9 (TLR-9), which is located at the endosomal inner membrane, thus prompting the maturation of the APC. Transferring the neoantigen from the endosome into the cytosol is a rate-limiting step in antigen cross-presentation. The present nanoparticle utilizes a pH-responsive polymer to facilitate the antigen endosomal escape. The pH-responsive polymer can enhance the endosomal escape of the BNP (possibly via a proton sponge effect), thereby transporting the cancer antigens to the cytosol, where they are processed by proteasomes, transported to the endoplasmic reticulum (ER), and finally loaded onto MHC I and presented to CD8+ T cells. In some embodiments, the pH-responsive polymer is itself an immune adjuvant. For example, when the pH-responsive polymer is PC7A, it may activate the stimulator of the interferon genes (STING) pathway, induce type I interferon secretion, and further promote the proliferation and maturation of natural killer (NK) cells and cytotoxic T lymphocytes (CTL). The present technology thus offers a simple and cost-effective approach to cancer immunotherapy that avoids complex and expensive procedures.

BRIEF DESCRIPTION OF THE DRAWINGS

FIG. 1B shows an illustrative embodiment wherein the polyplex core of the BNP includes a CpG, and the BNP is taken up via endocytosis into a dendritic cell. The pH responsive polymer, which becomes more positively charged in the endosome, allows for endosomal disassembly of the nanoparticles and escape from the endosome. The neoantigens (e.g., neoantigen peptides) are processed and displayed on the surface of the mature dendritic cell.

FIGS. 4A-4C show the following: 4A. Mean tumor volume curves comparing PBS control (i.e., VO), BNP alone, external beam radiation (EBRT) of 12 Gy alone, and BNP+12 Gy in a B78 melanoma model. 4B. Survival is compared between treatment groups. 4C. Individual mouse tumor growth curves for each treatment group.

FIG. 6A shows 100% of the mice in the B78 group rejected tumor rechallenge, compared to 0% of the naïve control mice. FIG. 6B shows 75% of the mice in the NXS2 group 75% of the mice treated with RT+BNP rejected tumor rechallenge, compared to 50% of the mice treated with BNP alone, and 15% among naïve control mice.

DETAILED DESCRIPTION

Figure 1A:
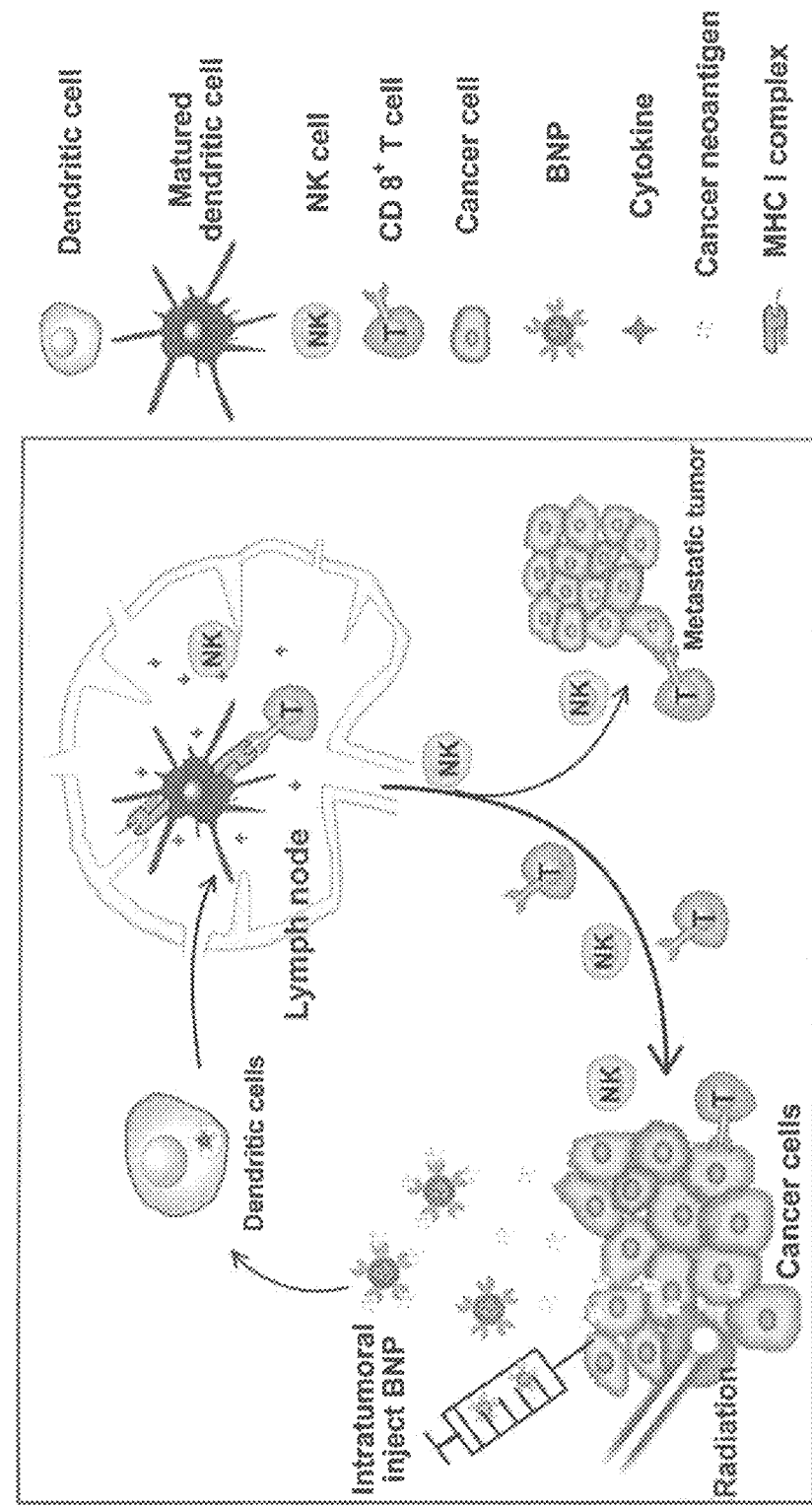
FIGS. 1A and 1B are schematics showing how an illustrative embodiment of the present technology may elicit an immune response. After radiation therapy, a BNP of the present technology is injected into a tumor (FIG. 1A). The BNP captures cancer neoantigens, presents them to dendritic cells, and induces the maturation and IFN secretion of dendritic cells (DCs). The matured DCs migrate to tumor-draining lymph nodes and activate T cells and NK cells.
Figure 1B:
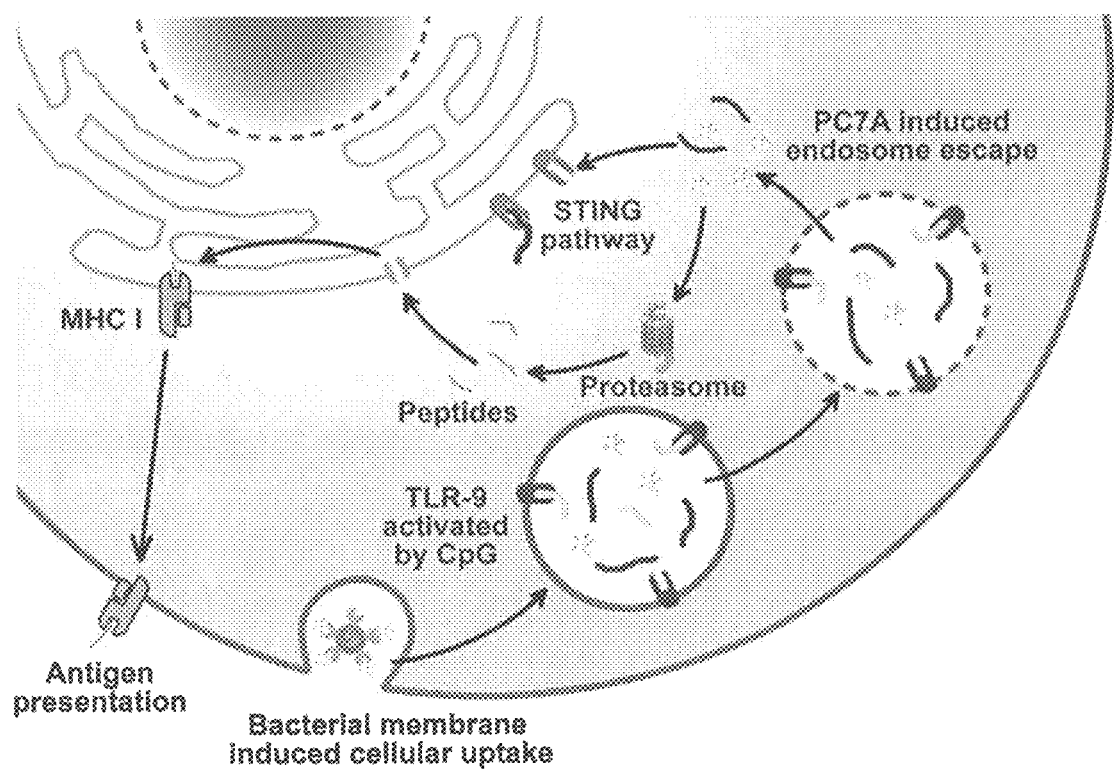

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "antigen capture groups" refer to chemical functional groups that react chemically with cancer antigens to covalently bind the antigens to the surface of nanoparticles of the present technology. In some embodiments, antigen capture groups may react with thiol groups or amine groups. For example, maleimide groups may react with thiols, 2-pyridinyldithio groups may react with thiols, and N-hydroxysuccinimide groups may react with amine groups on the cancer antigens.

As used herein, a "pH responsive polymer" is a synthetic polymer that includes ionizable amine groups and therefore may have a different net positive charge at alkaline pH versus acid pH values. pH responsive polymers of the present technology do not include naturally occurring proteins or polynucleic acids, but may include any biocompatible organic polymer that bears ionizable amine groups, e.g., primary, secondary, or tertiary amines, including cyclic or acylic amines. Cyclic amines (also referred to as "cycloamines" herein) are saturated, unsaturated or aromatic heterocycles having 5 to 8 ring members (monocyclic) or 9 to 10 ring members (bicyclic) in which the amine group is one of the ring members.

As used herein, an "anionic immune adjuvant" is a macromolecular compound or composition including such compound(s) bearing groups that are anionic or may ionize to become anionic, where the compound or composition potentiates or modulates a mammal's immune response to an antigen. The mammal may be, without limitation, a cat, dog, rodent, primate, or human.

As used herein, a "TLR 2 agonist" refers to ligands which bind toll-like receptor 2 as an agonist, i.e., upon binding, the ligands stimulate the innate immune response. Similarly, "TLR 4 agonist" refers to ligands which bind to toll-like receptor 4 as agonists and stimulate the innate immune response.

In one aspect, the present technology provides a nanoparticle comprising: a polyplex core comprising one or more pH-responsive polymers and one or more anionic immune adjuvants, wherein each pH-responsive polymer comprises ionizable amine groups; and a shell of bacterial cell membrane components at least partially coating the polyplex core, wherein the bacterial cell membrane components comprise TLR 2 and/or TLR 4 agonists.

A variety of pH-responsive polymers may be used as part of the core nanoparticle so long as the polymers contain ionizable amine groups. The pH-responsive polymers may be homopolymers or copolymers that are random or block copolymers. For example, the one or more pH-responsive polymers may be selected from the group consisting of polyacrylate esters, polymethacrylate esters, polyethyleneimines, polylysines, polyalkyleneguanidines, cationic dendrimers, and cationic N-substituted (polyamino acids). In any embodiments, the one or more pH-responsive polymers are selected from polyacrylate esters and/or polymethacrylate esters.

The molecular weight of the pH-responsive polymers may be any suitable weight that allows the core to form with an anionic immune adjuvant. Examples of suitable molecular weights (given as the weight average molecular weight) include 5 kDa, 10 kDa, 15, kDa, 20 kDa, 25 kDa, 30 kDa or a range between and including any two of the foregoing values (e.g., 5 kDa to 30 kDa or 15 kDa to 25 kDa).

The pH-responsive polymers include ionizable amine groups and are designed to enhance endosomal escape of the nanoparticle once taken up by a dendritic cell (antigen presenting cell) as an endosome. While not wishing to be bound by theory, by selecting a pH-responsive polymer that carries a higher charge at endosomal pH (e.g., 6.5) than at extracellular pH (e.g., 7-7.4), it is believed that the pH-responsive polymer will cause escape of the nanoparticle from the endosome. Thus, pH responsive polymers may exhibit a pKa from about 5.5 to about 7.5. Examples of suitable pKa values include 5.5, 5.7, 6.0, 6.3, 6.5, 6.8, 7.0, 7.3, 7.4 or any range between and including any of the foregoing values. In any embodiments, the ionizable amine groups may be an amino, acyclic alkylamine, and/or cyclic amine. For example, the ionizable amine may be —NRR' wherein R and R' are independently selected from H, and $C_{1-4}$ alkyl (e.g., methyl, ethyl, n-propyl, i-propyl, n-butyl, i-butyl, s-butyl, t-butyl). The cyclic amine group may be selected from $NH_2$, imidazolyl, pyrrolidinyl, piperidinyl and azepanyl groups. In any embodiment, the ionizable amine may be $NH_2$ and/or azepanyl. Thus, in any embodiments, the pH-responsive polymer may be PC7A.

The pH-responsive polymer is ion-paired with an anionic immune adjuvant to form the core of the nanoparticle. A variety of anionic immune adjuvants of various molecular weights (i.e., weight average molecular weights) and anionic charge levels may be used. The anionic immune adjuvant may include positively charged groups, but must carry a net negative charge under physiological conditions such that it will form a polyplex core with the pH-responsive polymer. For example, the anionic immune adjuvants may be a polynucleotide or polypeptide with a net negative charge. In some embodiments, the anionic immune adjuvant is selected from the group consisting of CpG oligodeoxynucleotide (referred to herein as "CpG" or "CpG ODN"), polyinosinic-polycytidylic acid, polyadenylic-polyuridylic acid, and polylactic-co-glycolic acid (PLGA).

In any embodiments, the anionic immune adjuvant may be a CpG. The CpG may have a weight average molecular weight of 4 to 8 kDa, including 5 to 7 kDa, or even 6 to 7 kDa. It is within the skill in the art to select a suitable CpG depending on the application at hand, including taking into account the species with which the nanoparticle is intended to be used. Thus, for example, CpG may be selected from CpG ODN 1585, 1826, 2216, 2336, 1668, 2006, 2007, BW006, D-SL01, 2395, M362, or D-SL03.

The weight ratio of pH responsive polymer to anionic adjuvant may vary and in any embodiment may be about 1:1 to about 20:1. For example, the weight ratio of pH responsive polymer to anionic adjuvant may be about 1:1, 1:1.5, 1:2, 1:2.5, 1:3, 1:4, 1:5, 1:10, 1:15, 1:20, or a range between and including any two of the foregoing values.

The polyplex core is coated at least in part with bacterial cell membrane components that include TLR 2 and/or TLR 4 agonists. The bacterial cell membrane components stabilize the polyplex core. The TLR 2 and/or TLR 4 agonists enhance uptake of the nanoparticle by antigen presenting cells (e.g., dendritic cells) and may optionally include pathogen-associated molecular patterns such as lipomannan and lipoarabinomannan. Bacterial cell membrane components from a variety of bacteria may be used such as (but not limited to) mycobacteria, *Listeria, Lactobacillus,* or *E. Coli* cell membrane components. In any embodiments, the cell membrane components may be *Mycobacterium smegmatis* or *Mycobacterium bovis Bacillus* Calmette-Guerin (BCG) cell membrane components.

While the shell of the nanoparticle can non-covalently bind cancer antigens, in any embodiment, the shell may further include antigen capture groups. The latter groups enhance the adaptive immune response by ensuring more cancer antigens are covalently bound to the surface of the nanoparticle. In any embodiments, the antigen capture groups include maleimide groups, 2-pyridinyldithio groups, or N-hydroxysuccinimide groups.

The nanoparticles of the present technology generally have a hydrodynamic diameter below 1 μm. In any embodiments, the hydrodynamic diameter of the present nanoparticles may be about 60 to about 900 nm, e.g., about 100 to about 900 nm or even about 100 nm to 400 nm. In any embodiments the hydrodynamic diameter may be about 60, about 100, about 150, about 200, about 250, about 300, about 350, about 400, about 500, about 600, about 700, about 800, about 900 nm or a range between and including any of the foregoing values.

In another aspect, there are provided methods of making BNPs of the present technology. The polyplex core of the BNP may be made by mixing an aqueous solution of a pH-responsive polymer (including without limitation any of those described herein) with an anionic immune adjuvant (including without limitation, any of those described herein). The bacterial cell membrane components (e.g., in an extract of the selected bacteria) may be coated onto the polyplex at pH 7 or above (e.g., 7.4).

In another aspect, the present technology provides a kit including any of the nanoparticles described herein, as well as compositions comprising any of the nanoparticles disclosed herein and a pharmaceutically acceptable carrier.

The compositions may be used in the methods described herein. In one aspect the present technology provides a method for stimulating an immune response in a mammal. The methods may include administering an effective amount of a nanoparticle of any embodiment described herein to an irradiated tumor in the mammal, wherein the radiation was an amount effective to release cancer antigens from the tumor and stimulate the immune response. In any embodiment of the methods, the nanoparticle may be injected into the tumor. "Effective amount" refers to the amount of nanoparticle required to produce a desired effect. One example of an effective amount includes amounts or dosages that produce the desired immune response, including, but not limited to, causing a tumor to grow more slowly, stop growing or even shrink in size. Where the cell is in vivo, the effective amount is delivered to a subject, e.g., a subject in need thereof. As used herein, a "subject" is a mammal, such as a cat, dog, rodent or primate. In some embodiments, the subject is a human.

The compositions described herein are formulated for administration to the target tumor. Depending on the location of the tumor, the present compositions may be formulated for various routes of administration, for example, by parenteral, intravitreal, intrathecal, intracerebroventricular, rectal, nasal, vaginal administration, direct injection into the target tumor, or via implanted reservoir. Parenteral or systemic administration includes, but is not limited to, subcutaneous, intravenous, intraperitoneal, and intramuscular injections. In some embodiments, the present compositions are formulated for direct injection into the tumor or into the tissue containing the tumor. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the nanoparticles described herein. Injectable forms may be prepared with acceptable solvents or vehicles including, but not limited to sterilized water, phosphate buffer solution, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remington's Pharmaceutical Sciences" Mack Pub. Co., New Jersey (1991), which is incorporated herein by reference. Exemplary carriers and excipients may include but are not limited to USP sterile water, saline, buffers (e.g., phosphate, bicarbonate, etc.), tonicity agents (e.g., glycerol).

Specific dosages may be adjusted depending on conditions of disease, the age, body weight, general health conditions, sex, and diet of the subject, dose intervals, administration routes, excretion rate, and combinations of drug conjugates. Any of the above dosage forms containing effective amounts are well within the bounds of routine experimentation and therefore, well within the scope of the instant present technology. By way of example only, such dosages may be used to administer effective amounts of the present nanocapsules to the patient and may include 0.1, 0.2, 0.3, 0.4, 0.5, 0.75, 1.0, 1.5, 2.0, 2.5, 3.0, 4.0, 5.0, 6.0, 7.0, 8.0, 9.0, 10, 11, 12, 13, 14, 15 mg/kg or a range between and including any two of the forgoing values such as 0.1 to 15 mg/kg. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

In another aspect, the present technology provides kits including the components needed to prepare any of the compositions described herein. For example, a kit may include a package containing a nanoparticle as described herein and directions for use of the kit. In another embodiment, the kit includes pH responsive polymer, anionic immune adjuvant, and bacterial cell membrane components of any embodiment of the present technology as well as directions for preparing the nanoparticle.

The examples herein are provided to illustrate the advantages of the present technology and to further assist a person of ordinary skill in the art with preparing or using the nanoparticle compositions of the present technology. To the extent that the compositions include ionizable components, salts such as pharmaceutically acceptable salts of such components may also be used (e.g., alkali metal salts (including but not limited to sodium and potassium salts), halide salts (including but not limited to chloride and bromide salts), and the like. The examples herein are also presented in order to more fully illustrate the preferred aspects of the present technology. The examples should in no way be construed as limiting the scope of the present technology, as defined by the appended claims. The examples can include or incorporate any of the variations or aspects of the present technology described above. The variations or aspects described above may also further each include or incorporate the variations of any or all other variations or aspects of the present technology.

EXAMPLES

Materials and Methods.

ODN 1826 (Type B) endotoxin-free (sterile) (CpG oligonucleotide) was purchased from Innaxon (San Diego, Calif., USA). Mal-PEG4-NHS was purchased from Conju-Probe (San Diego, Calif., USA). Methacryloyl chloride was purchased from Alfa Aesar (Tewksbury, Mass., USA). 1H-azepine-1-ethanol, hexahydro- was purchased from Chemscene LLC (Princeton, N.J., USA). Cy5.5 dye was obtained from Lumiprobe Corporation (Hallandale Beach, Fla., USA). *Mycobacterium smegmatis* mc$^2$ 155 strain was kindly donated by Prof. Adel M. Talaat, and was grown in Middlebrook 7H9 broth (HiMedia, West Chester, Pa., USA). Ovalbumin from chicken egg white (Ova) and all solvents were purchased from Sigma-Aldrich (St. Louis, Mo. USA) without further purification. Other reagents were purchased from Thermo Fisher Scientific (Fitchburg, Wis. USA) and used as received unless otherwise stated.

Figure 2:
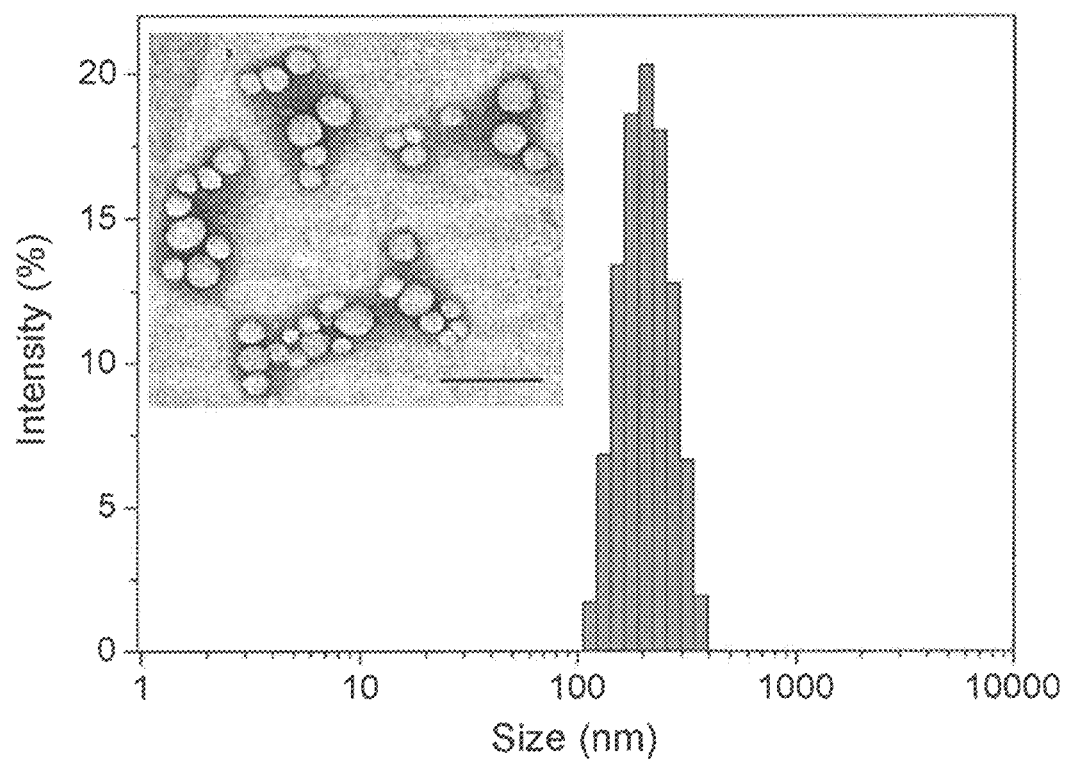
FIG. 2 shows the size (as characterized by dynamic light scattering) and morphology (tunneling electron microscopy) of an illustrative embodiment of the present nanoparticles. Scale bar for TEM is 500 nm.

$^1$H NMR spectra of all intermediate and final polymer products were recorded on a Bruker 400 spectrometer in CDCl$_3$ at 25° C. Molecular weights (Mn and Mw) and polydispersity indices (PDI) of the polymers were determined by a gel permeation chromatographer (GPC) equipped with a refractive index detector, a viscometer detector, and a light scattering detector (Viscotek, USA). DMF with 10 mmol/L LiBr was used as the mobile phase with a flow rate of 1 mL/min. The sizes and morphologies, as well as the zeta potential, of the polyplexes and nanoparticles were studied by dynamic light scattering (DLS, Zeta-Sizer Nano ZS90, Malvern Instruments, USA) and transmission electron microscopy (TEM, Philips CM200 Ultra Twin) (FIG. 2).

For all flow cytometry and PCR experiments statistical significance between groups was determined with a two-way analysis of variance (ANOVA) test followed by a Tukey's post hoc comparisons test. For survival analysis, Kaplan-Meier curves were generated, and a Log-rank test was performed to find any overall differences between all survival curves. Then cox regression analysis or individual Log-rank tests with Bonferroni corrections for multiple comparisons were performed to determine differences between individual groups. For contingency testing for immune memory, a Chi-square test was performed to determine the statistical significance between groups. Analyses were performed on GraphPad Prism 7.04. Tumor growth curves were compared using a linear mixed-effects model, including random intercepts for subjects, followed by Tukey's post hoc comparisons. The tumor volumes were log transformed to account for the log-linear growth pattern. Analyses were performed in R 3.5.0 using the NLME package.

Example 1. Synthesis of PC7A Polymer

Synthesis of Methacrylate Monomer.

The monomer 2-(hexamethyleneimino) ethyl methacrylate (C7A-MA) was synthesized according to previous reports (K. J. Zhou, Y. G. Wang. X. N. Huang, K. Luby-Phelps, B. D. Sumer, J. M. Gao, *Angew Chem Int Edit* 2011, 50, 6109). Briefly, 1H-azepine-1-ethanol, hexahydro- (5.0 g, 34.5 mmol) and triethylamine (TEA, 7.0 g, 69 mmol) was dissolved in 100 mL dried THF and cooled to 0° C. in an ice bath. Methacryloyl chloride (4.0 g, 38.5 mmol) was dissolved in 15 mL dried THF and slowly dropped into the previous solution. The reaction was moved to room temperature and stirred for 8 h, then filtered to remove TEA salt. The filtrate was condensed by rotary evaporation and further purified by flash chromatography (Hex:EtOAc=2:1). C7A-MA: $^1$H NMR (TMS, CDCl$_3$, ppm): 6.1 (s, 1H), 5.6 (s, 1H), 4.2 (t, 2H), 2.8 (s, 2H), 2.7 (s, 4H), 2.0 (s, 3H), 1.8 (s, 4H), and 1.6 (s, 4H).

The monomer 2-(tert-butoxycarbonylamino) ethyl methacrylate (BocN-MA) was synthesized followed a similar procedure. BocN-MA: $^1$H NMR (TMS, CDCl$_3$, ppm): 6.1 (s, 1H), 5.6 (s, 1H), 4.2 (t, 2H), 3.5 (q, 2H), 2.7 (s, 4H), 2.0 (s, 3H), and 1.4 (s, 9H).

Synthesis of PC7A Polymer.

The PC7A polymer was synthesized by atom transfer radical polymerization (ATRP) initiated by ethyl 2-bromoisobutyrate. C7A-MA (0.5 g, 2.37 mmol), CuBr (8.5 mg, 59 nmol), and initiator (11.6 mg, 59 nmol) were dissolved in 0.5 mL dried THF. After three cycles of freeze-pump-thaw, PMDETA (10.3 mg, 59 nmol) was added. The polymerization was carried out at 70° C. for 10 hrs. The reaction mixture was solved in acidic water (pH 4) and dialyzed (cut-off molecular weight, MWCO 3500 Da) in distilled water to remove unreacted monomer and copper. The product was obtained by lyophilization and characterized by gel permeation chromatography (GPC) and $^1$H NMR.

PC7A: $^1$H NMR (TMS, CDCl$_3$, ppm): 4.0 (s, 2H), 2.8 (s, 2H), 2.7 (s, 4H), 1.8 (br, 2H), 1.6 (br, 8H), and 0.8-1.1 (br, 3H).

Synthesis of Cy5.5 fluorescent-tagged PC7A polymer.

PC7A polymer with 5% amine groups was synthesized following the same ATRP procedure with the addition of 5% BocN-MA monomer. The product was deprotected in 5M HCl for 5 h.

PC7A-NH$_2$ polymer (10 mg) was dissolved in 300 μL DMSO, and subsequently, 6.5 μL TEA and 0.1 mg Cy5.5-NHS were added to this solution. The reaction was kept in darkness and at room temperature for 8 h, and then dialyzed (MWCO 3500 Da) and lyophilized to obtain the product. PC7A-Boc: $^1$H NMR (TMS, CDCl$_3$, ppm): 4.1 (s, 2.1H), 3.4 (s, 0.1H), 2.8 (s, 2H), 2.7 (s, 4H), 1.8 (br, 2.1H), 1.6 (br, 8H), 1.4 (s, 0.45H), and 0.8-1.1 (br, 3.15H). PC7A-NH$_2$, $^1$H NMR (TMS, CDCl$_3$, ppm): 4.1 (s, 2.1H), 3.0 (s, 0.1H1), 2.8 (s, 2H), 2.7 (s, 4H), 1.8 (br, 2.1H), 1.6 (br, 8H), and 0.8-1.1 (br, 3.15H).

Example 2. Bacteria Growth and Membrane Extraction

*M. smegmatis* (strain mc$^2$ 155) was grown in Middlebrook 7H9 broth with the addition of a 10% (vol/vol) FD019 supplement at 37° C. with aeration and shaking. Cells were harvested at an OD600 of around 3, collected with a 4000 G centrifuge, and washed twice with distilled water.

The bacterial membrane was extracted as follow. A ~2 g bacteria pellet was dispersed in 40 mL Tris HCl buffer (20 mM, pH 8.0) containing 15 mg/mL lysozyme. It was incubated in a 37° C. shaker for 3 h. After adding 400 mg SDS, the cells were further broken down with a probe sonicator in an ice bath for 10 min and then lyophilized. The dried bacteria lysate was suspended in a chloroform-methanol-water solution (CMW; 30:15:1, v/v/v), placed on a shaker at 37° C. for 1 h, and then filtered by Millipore HVLP Durapore® membrane (0.45 gun). The residue was extracted by CMW two more times and then the filtrate was combined and dried under vacuum. The bacterial membrane was dispersed in PBS and the protein concentration was determined using the BCA test. The membrane was extruded using a mini extruder (Avanti Polar Lipids Inc., Alabaster, Ala., USA) through a 0.4 μm polycarbonate membrane filter (Whatman® Nuclepore™ Track-Etched Membranes) 21 times before use.

Example 3. Preparation of the BNP

Preparation and characterization of PC7A/CpG polypex.

Polyplex was freshly prepared by adding the polymer solution at different concentrations (1:1, 2.5:1, 5:1, 10:1, 20:1) into 1.2 mg/mL CpG solution (1:1, v/v). The mixture was vortexed for 10 seconds and incubated at room temperature for 15 min before use. Agarose gel electrophoresis was employed to optimize the PC7A to CpG weight ratios at different pHs (6.5, 7.4) using a 1% agarose gel in a TAE (Tris-acetate-EDTA) buffer solution with a current of 110 V for 30 min. The retardation of the complexes was stained by Sybr safe and visualized on a UV illuminator (Bio-Rad Baloratories, Inc., Hercules, Calif., USA). Based on the electrophoresis results (data not shown), CpG was completely complexed at a pH of 7.4 when the polymer/CpG weight ratio reached 2.5 and above.

Preparation and Characterization of BNP.

Seven microliters of a 1.5M sodium carbonate solution and 100 μL freshly prepared polyplex solution (containing 400 μg PC7A and 60 μg CpG) were sequentially added into 100 μL bacterial membrane solution (containing 400 μg protein), vortexed, and extruded through a 0.2 μm polycarbonate membrane filter 21 times. Twenty microliters of Mal-PEG4-NHS solution (6.4 mg/mL) was then added. The mixture was incubated at room temperature for 1 h, yielding the final BNP product which was stored at 4° C. before use. The encapsulation efficiency was tested on a NanoDrop spectrophotometer. Typically, PC7A containing 10% polymer tagged with Cy5.5 was used to form a polyplex with CpG, and then coated with bacterial membrane by extrusion. To determine the encapsulation efficiency of the polyplex, a NanoDrop spectrophotometer was used to measure its adsorption intensity at 675 nm before and after extrusion. Finally, DLS and TEM were employed to test its size, zeta potential, and morphology.

pH Titration.

PC7A/hyaluronic acid polyplexes were formed by mixing the PC7A solution (50 mg PC7A in 25 mL DI water) with a hyaluronic acid solution (15 mg in 25 mL DI water). Thereafter, an excessive amount of 0.1 M HCl (e.g., 3 mL) was added into the polyplex solution to fully protonate the PC7A. The pH titration was performed by adding small volumes of 0.02 M NaOH solution under stirring. Meanwhile, the pH value of the polyplex solution was monitored using an Accumet AB 15 pH meter with an InLab microelectrode to determine the pH value as a function of the protonation degree of the tertiary amines in PC7A. The critical points of complete protonation and deprotonation of PC7A in the figure (pH 5.14 and 8.43, indicating 100% and 0% protonation degree) were determined by the two maximum values of the $1^{st}$ derivative of this function.

In Vitro Antigen Capture Capability.

Figure 3A:
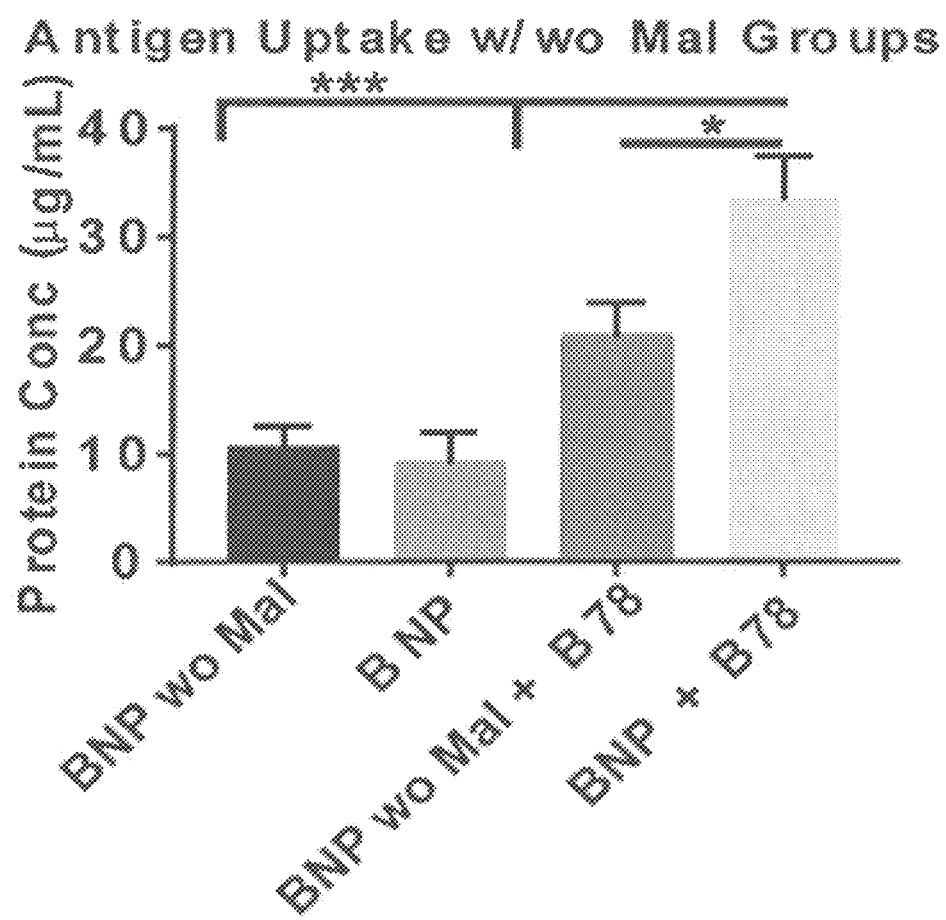
FIG. 3A is a bar graph showing quantification of the total protein for an illustrative embodiment of present nanoparticles as described in Example 3 after they were incubated with cancer cell lysate.

To test the capacity of BNP to capture neoantigens, BNP was incubated with or without (w/wo) Mal with tumor lysate in vitro. 1 mL BNP solution with or without Mal groups (containing 1 mg protein) were mixed with 5 mL B78 melanoma cell lysate and incubated at 37° C. for 4 h. The samples were then dialyzed for 24 h within a dialysis bag (MWCO: 100,000 Da). The samples were diluted 100 times and their protein concentration was determined using a BCA test. BNP w/wo Mal could adsorb proteins from tumor lysate; however, BNP with Mal showed significantly higher levels of protein adsorption (FIG. 3A).

Endo/Lysosomal Rupture.

Figure 3B:
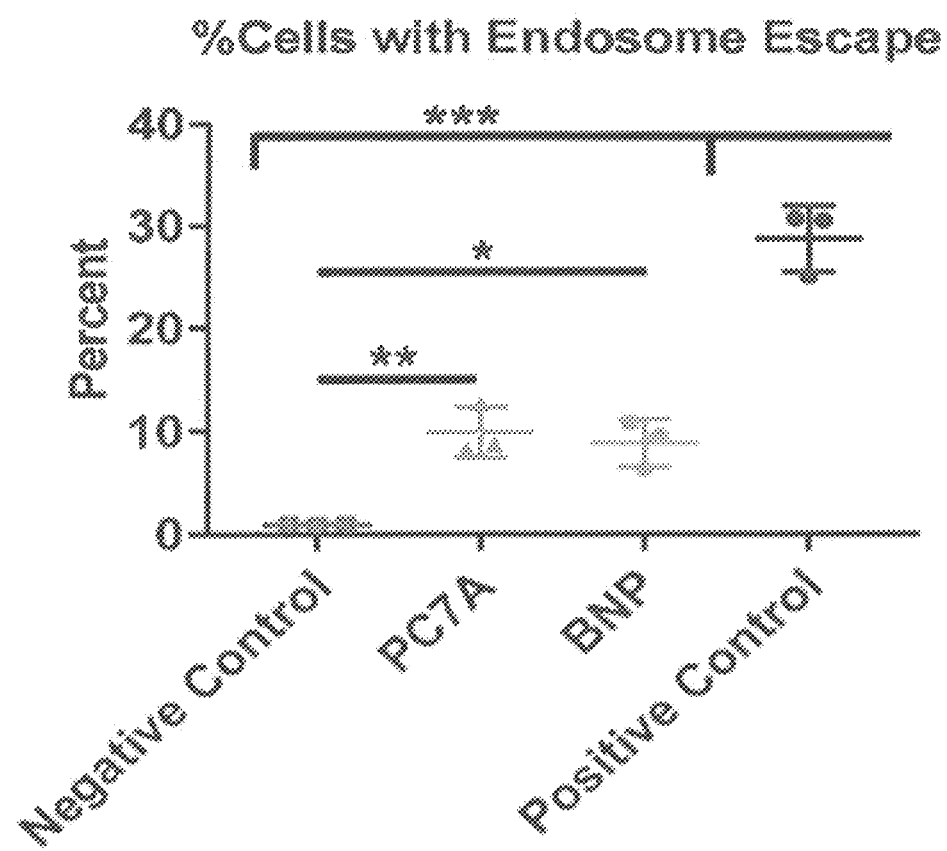
FIG. 3B is a graph of PC7A alone or as a part of BNPs, which enhanced the percentage of endosomal disruption compared to the untreated negative control (shown as a percent of total cells, however this effect may be diluted due to lack uptake into all cells) as described in Example 3. PET was used as a positive control

B78 cells were plated onto a tissue-culture-treated 96-well plate and treated with PC7A, BNP, or polyethylenimine (PEI) for 12 h. Subsequently, B78 cells were incubated with acridine orange (ThermoFisher, diluted 1:20,000) for 4 h, which accumulates in intact endo/lysosomes. The acridine orange signal was assessed using flow cytometry with 488 nm excitation and 650-690 nm emission (Attune, Thermo-Fisher). Once endocytosed by DCs, the BNP confocal laser scanning microscopy (CLSM) images demonstrated incomplete co-localization of BNP with acridine orange staining endosomal compartments (FIG. 3B). This is consistent with endosomal escape, perhaps reflecting disruption of endosomal compartments in cells taking up BNP uptake, resulting from the pH-responsive nature of the PC7A polymer.

DC Activation by BNP.

Figure 3C:
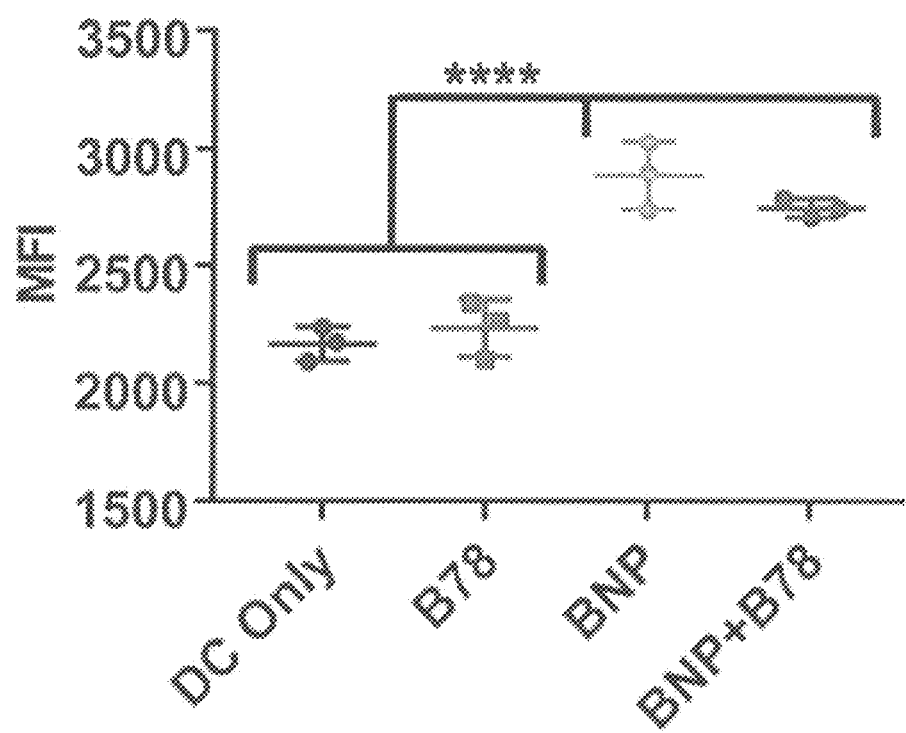
FIGS. 3C-3E are graphs of endosomal disruption according to Example 3. Cells negative for acridine orange staining were indicative of cells with ruptured endosomes and/or lysosomes as measured by flow cytometry. DCs incubated with BNPs w/wo B78 lysate demonstrate the presence of significantly increased activation markers including CD80 (FIG. 3C), CD86 (FIG. 3D), and CD40 (FIG. 3E).
Figure 3D:
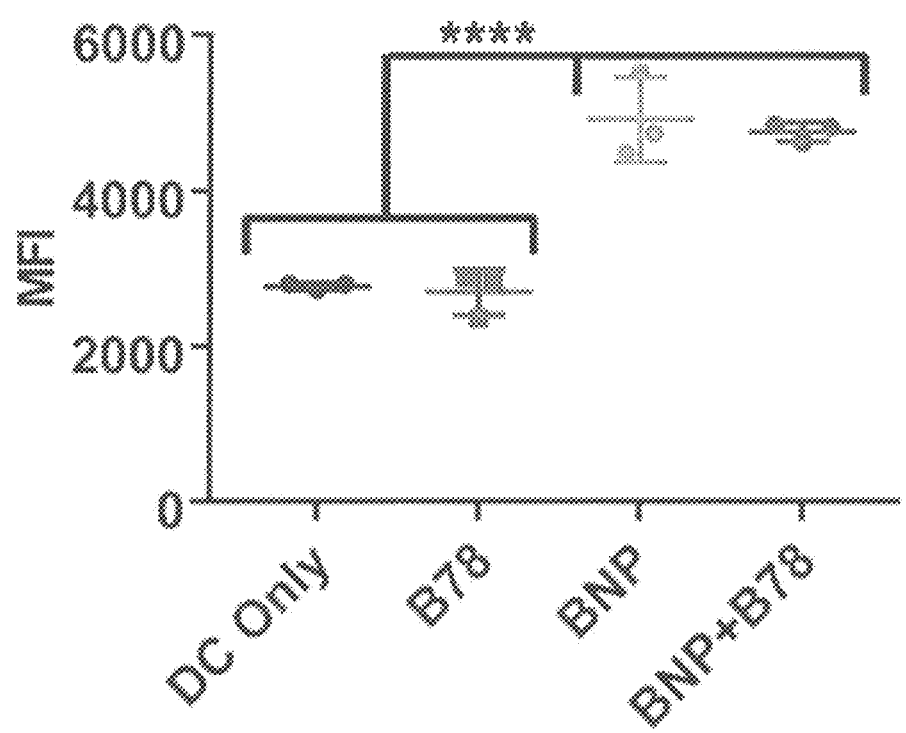
Figure 3E:
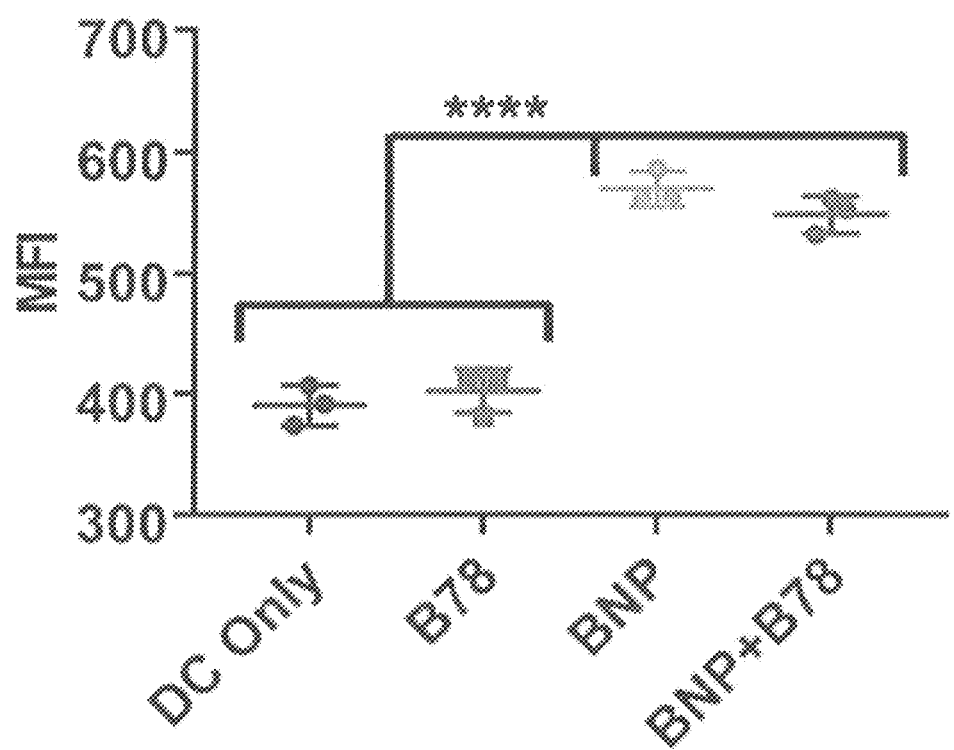

Using in vitro co-culture, it was tested whether BNP can activate DCs, either alone or when adsorbed with tumor lysate. Consistent with an effective stimulation of DCs following exposure to BNP, increased expression of DC activation markers CD80, CD86, and CD40 was observed, regardless of the presence of tumor lysate (FIG. 3C-3E).

Dendritic Cell Uptake/Activation Studies.

It was determined whether BNP could enhance the uptake of adsorbed neoantigens into dendritic cells (DCs). DCs were isolated from spleens of C57BL/6 mice and cultured in B78 media (recipe as listed above) additionally supplemented with 1% HEPES, 2 µM 2-mercaptoethanol (Sigma-Aldrich), and 200 ng/mL FLT3 ligand (PeproTech). Ova were tagged with fluorescent dyes (FITC or Cy5-NHS ester) in PBS at a concentration of 1 mg/mL and a protein/fluorophore molar ratio of 1:1.2 for 24 h, and then dialyzed 24 h in PBS (MWCO: 8,000 Da) and preserved at −20° C. before use. For uptake studies, DCs were incubated with free FITC-Ova or BNP pre-mixed with FITC-Ova for 12 h at 37° C. Uptake was measured by mean fluorescence intensity (MFI) of FITC signal in CD11C+, MHCII+ cells via flow cytometry (Attune, ThermoFisher). For DC uptake imaging, DCs were incubated with free Cy5-Ova or BNP mixed Cy5-Ova for 12 h, stained with Hoechst 33342 (nuclei) and Lysotracker green (endo/lysosomes), and then imaged with a Nikon A1R-Si high speed spectral laser scanning confocal inverted microscope (Nikon, Melville, N.Y.). Activation of DCs was measured by MFI changes of CD80, CD86, or CD40 in CD11C$^+$, MHCII$^+$ DCs that were incubated with BNP, BNP+B78 lysate, or B78 lysate alone for 12 h. All antibodies used for flow cytometry are listed in Table 1.

TABLE 1

Antibodies and markers used for flow cytometry.

| Antibody/Marker | Fluorophore | Clone | Company |
|---|---|---|---|
| Innate Panel | | | |
| Live/dead | GhostRed 780 | | Tonbo Biosciences |
| CD45 | FITC | 30-F11 | Tonbo Biosciences |
| CD11b | V450 | M1/70 | BD Biosciences |
| CD103 | PE-Cy7 | 2E7 | Biolegend |
| MHC II (I-A/I-E) | BV510 | M5/114.15.2 | BD Biosciences |
| CD11c | BB700 | HL3 | BD Biosciences |
| Adaptive Panel | | | |
| Live/dead | GhostRed 780 | | Tonbo Biosciences |
| CD45 | BV510 | 1M7 | BD Biosciences |
| CD25 | BB515 | PC61 | BD Biosciences |
| CD4 | BV785 | GK1.5 | Biolegend |
| CD8 | APC-R700 | 53-6.7 | BD Biosciences |
| 41BB | BV421 | 1AH2 | BD Biosciences |
| FoxP3 | PE-Cy7 | FJK-16s | ThermoFisher |

Figure 3F:
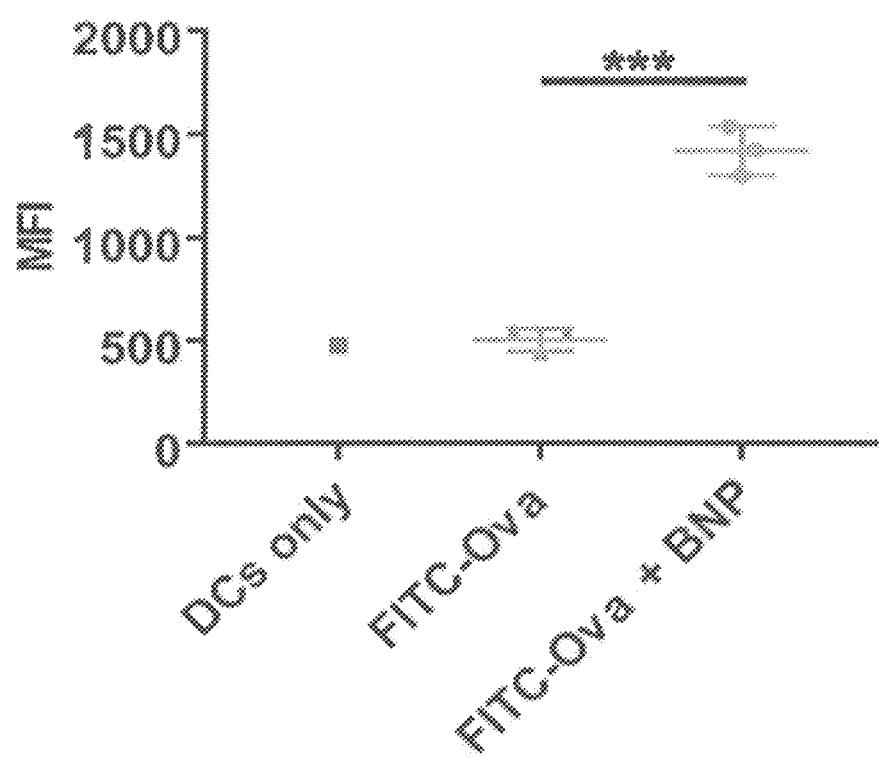
FIG. 3F is a graph showing BNP enhanced Ova (mock neoantigen) uptake in DCs quantified by flow cytometry according to Example 3. (N=3, Significance determined by t-test (C) or two-way ANOVA (B, G-J) with Tukey multiple comparisons test, *P<0.05, P<0.01, *P<0.001, ****P<0.0001, all error bars expressed as a standard error of the mean (SEM)).

Ova adsorbed onto BNP exhibited greater uptake into DCs compared to free Ova, demonstrating that BNP can enhance both antigen absorption as well as uptake into APCs (FIG. 3F).

Example 4. In Vivo Mouse Studies

Cell Lines:

The B78-D14 cell line us derived from B16 melanoma and was obtained from Ralph Reisfield (Scripps Research Institute) in 2002. The NXS2 cell is a murine neuroblastoma hybrid cell line obtained from Alice Yu. B78 and NXS2 cells were grown in RPMI 1640 or DMEM (Mediatech), respectively, supplemented with 10% fetal bovine serum (FBS), 2 mM L-glutamine, 100 U/mL penicillin and 100 µg/mL streptomycin. Cells were maintained in culture below 80% confluence for all passages and early passages (3-8) were used for all experiments. Cell authentication was performed per ATCC guidelines using morphology, growth curves, and mycoplasma testing within 6 months of use.

Murine Tumor Models:

To examine the effects of treatment with RT+BNP in an in vive tumor microenvironment (TME), well-established B78 melanoma or NXS2 neuroblastoma tumors engrafted in syngeneic mice were treated with placebo (intratumoral (IT) PBS), RT, IT BNP, or RT+IT BNP. All in vive animal studies were conducted under an approved institutional animal care and use committee protocol. Female mice aged 6-8 weeks were purchased from Taconic (C57BL/6, B78) or Jackson (A/J, NXS2). Both B78 and NXS2 tumors were engrafted by subcutaneous flank injection of 2×10$^6$ cells. Tumor size was tracked using caliper measurements twice weekly and volume was approximated as (width$^2$×length)/2. Mice were randomized to have a median size of 100-150 mm$^3$ prior to treatment. Samples sizes for each experiment were calculated based on preliminary data to have an 80% power to detect a difference between treatment groups at a two-sided significance level of 0.05. Treatment started on Day 1 after randomization and tumor growth was tracked till Day 30 or a predetermined tumor sacrifice point due to tumor burden. Survival was tracked to Day 60 and all mice with complete response were rechallenged with 2×10$^6$ B78 cells on the contralateral flank at Day 90 and compared to naïve controls to test for immune memory. All mouse studies were repeated in duplicate and final replicates are presented for tumor response and aggregate data for survival.

Treatments.

Treatment consisted of external beam radiation of 12 Gy delivered on Day 1 with an Xrad320 (PXi) irradiator with the tumor exposed and the rest of the animal shielded with lead blocks. Nanoparticle injections of either whole nanoparticles or different components including CpG, PC7A-HA, Bacterial membrane alone, BNP without mal, or full BNP were injected intratumorally on Days 1,3,5,7,9. Each injection of BNP contained 100 µg of bacterial membrane, 100 µg PC7A, 15 µg CpG, 32 mg of Mal-PEG4-NHS.

Flow Cytometry of Immune Cell Infiltrates.

Tumors were dissected on Day 7 from B78 mice treated with RT on Day 1 and BNP on Day 1, 3, and 5. Tumors were disassociated with DNAse and collagenase on a Miltenyi GentleMACS. Disassociated cells were stained with innate and adaptive immune cell antibody panels (see Table 1) and analysis of flow data was performed on FCS Express using gating strategies.

Gene Expression.

The tumor gene expression effects of BNP, RT, or combination RT+BNP by using quantitative real-time PCR were determined. Relative mRNA transcript expression from tumor specimens was quantified via real-time PCR using a Bio-Rad iQ5 RT-qPCR Detection System and Power SYBR Green PCR Master Mix (Life Technologies). PGK and HPRT were used as endogenous housekeeping genes that have been confirmed to have a stable expression with radiation (G. Iyer, A. R. Wang, S. R. Brennan, S. Bourgeois, E. Armstrong, P. Shah, P. M. Harari, Sci Rep 2017, 7, 43763). Fold changes after treatments were normalized to placebo (PBS)-treated control samples. RNA isolation and reverse transcription procedures have been previously described (L. R. Werner, J. S. Kler, M. M. Gressett, M. Riegert. L. K. Werner, C. M. Heinze, J. G. Kern, M. Abbariki, A. K. Erbe, R. B. Patel, R. N. Sriramaneni, P. M. Harari, Z. S. Morris, Radiother Oncol 2017, 124, 418), and a list of all targets and detailed primer information are provided in Table 2.

TABLE 2

List of primers used for qPCR.

| | | |
|---|---|---|
| Arg-1 | Forward | ACA TTG GCT TGC GAG ACG TA |
| | Reverse | ATC ACC TTG CCA ATC CCC AG |
| Ccl2 | Forward | TTT GAA TGT GAA GTT GAC CCG T |
| | Reverse | GTG CTT GAG GTG GTT GTG GA |
| Ccl20 | Forward | CGA CTG TTG CCT CTC GTA CA |
| | Reverse | AGC TTC ATC GGC CAT CTG TC |
| Ccl3 | Forward | ACA TCA TGA AGG TCT CCA CCA C |
| | Reverse | CCA TAT GGC GCT GAG AAG ACT |
| Ccl4 | Forward | CCT CCC ACT TCC TGC TGT TT |
| | Reverse | GTC TCA TAG TAA TCC ATC ACA AA |
| Ccl5 | Forward | GAA GGA ACC GCC AAG TGT GT |
| | Reverse | CCT AGC TCA TCT CCA AAT AGT TGA T |
| Cxcl10 | Forward | CGC TGC AAC TGC ATC CAT A |
| | Reverse | TAG GCT CGC AGG GAT GAT TTC |
| Cxcl11 | Forward | TGT GAC ATC CTG GGA ACG TCT |
| | Reverse | TTC CAA GAC AGC AGA GGG TCA |
| Cxcl9 | Forward | CGC TGT TCT TTT CCT CTT GGG |
| | Reverse | CCT TAT CAC TAG GGT TCC TCG AA |
| Foxp3 | Forward | GAC CCC CTT TCA CCT ATG CC |
| | Reverse | GGC GAA CAT GCG AGT AAA CC |
| Icam1 | Forward | GTC GAG GGT TTC TCT ACT GGT |
| | Reverse | GAA CCA CTG CCA GTC CAC ATA G |
| Ido-1 | Forward | GTG GGC TTT GCT CTA CCA CA |
| | Reverse | AAG CTG CCC GTT CTC AAT CA |
| Ifnar | Forward | GAA CAA AAG ACG AGG CGA AG |
| | Reverse | CCC TTC CTC TGC TCT GAC AC |
| Ifnβ | Forward | TCC ACC AGC AGA CAG TGT TTC |
| | Reverse | TCA AGT GGA GAG CAG TTG AGG |
| Il-10 | Forward | GCA TGG CCC AGA AAT CAA GG |
| | Reverse | GAG AAA TCG ATG ACA GCG CC |
| Il-1α | Forward | CGT CAA AGA TGT CCA ACT TCA CC |
| | Reverse | TCT TCC CGT TGC TTG ACG TT |
| Il-1β | Forward | TGA TTC AAG GGG ACA TTA GGC A |
| | Reverse | ACC AAT TCA TCC CCC ACA CG |
| Il-6 | Forward | CTC TGC AAG AGA CTT CCA TCC A |
| | Reverse | AAG TAG GGA AGG CCG TGG TT |
| Irf3 | Forward | TGG TAG ACA GGG TAG AAG CCA |
| | Reverse | TGA GAC AGC TGG CAC CTT GA |
| Irf5 | Forward | ACC ACG GAG TCC AAT TAC CC |
| | Reverse | ACT CCT TGG CAG GTT TTG CTA |
| Mhc1-h2kb | Forward | AGA AGT GGG CAT CTG TGG TG |
| | Reverse | GAC AAC CAG AAC AGC AAC GG |
| Mx-1 | Forward | CGG CCC TGT ATT GAC CTC AT |
| | Reverse | ACT CCA GAC AGT GCT TCC AG |
| Nfkβ | Forward | GAC CTG TAT CAG ACA CCT CT |
| | Reverse | CTG TCG TGT CCT TCT TTG G |
| Oas2 | Forward | TAA GAG GCT GCT CCG ATG GT |
| | Reverse | GAC GTC AAG GTA TGC ATC TTG GT |
| Oas3 | Forward | TTT CTC AGT CAA AGG CGT CCA |
| | Reverse | TCT ATC AG TGT TCT CCG TCT G |
| Pdl-1 | Forward | CCA GCC ACT TCT GAG CAT GA |
| | Reverse | CTT CTC TTC CCA CTC ACG GG |
| Igfβ | Forward | CTA TTG CTT CAG CTC CAC AG |
| | Reverse | GAC AGA AGT TGG CAT GGT AG |
| Tnfrsf10b | Forward | GAT CCC GAA AGT GCG AAC TC |
| | Reverse | TAC CGG AAC CAG CAA CTT CT |
| Tnfα | Forward | TTC TGC AAA GGG AGA GTG GTC |
| | Reverse | TGA AGG TAG GAA GGC CTG AGA T |
| Vcam1 | Forward | AAC ACT CTT ACC TGT GCG CT |
| | Reverse | TCA GGG AAT GAG TAG ACC TCC A |

Results

Flow cytometry.

Flow cytometry analyses of disaggregated tumors treated with RT+BNP showed significantly increased populations of basic leucine zipper transcription factor ATF-like 3 (batF3) DCs compared to all other groups (data not shown). Groups treated with BNP showed increased levels of activated $CD25^+$ and $41BB^+$ effector $CD8^+$ T cells compared to the PBS or RT only groups (data not shown). In comparison, tumors treated with RT had increased activation of $CD4^+$ T helper cells (data not shown). However, with RT alone, the majority of activated $CD4^+$ T cells were suppressive Tregs ($CD4^+$ $CD25^+$ $FoxP3^+$), while in the RT+BNP group no increase in Treg infiltrate was observed (data not shown).

Gene Expression.

In tumors treated with RT, increased expression of interferon-beta (Ifnβ) was observed (a marker of STING pathway activation) as well as other interferon response genes such as Mx1, Oas2, and Oas3 (L. Galluzzi, C. Vanpouille-Box, S. F. Bakhoum, S. Demaria, Cell 2018, 173, 276). Mhc1, which is necessary for effector T cell recognition of tumor cells, trended towards an increase in the RT+BNP group compared to RT or BNP treatments alone. Gene expression studies also demonstrated activation of innate immune pathways such as the Nf-κβ pathway and the Tnfα pathway with RT+BNP treatment. However, expression of innate immunosuppressive enzymes, Indoleamine-2,3-dioxygenase (Ido1) and Interleukin-10 (1110) were also increased with combination RT+BNP treatment.

BNP Efficacy.

Figure 4A:
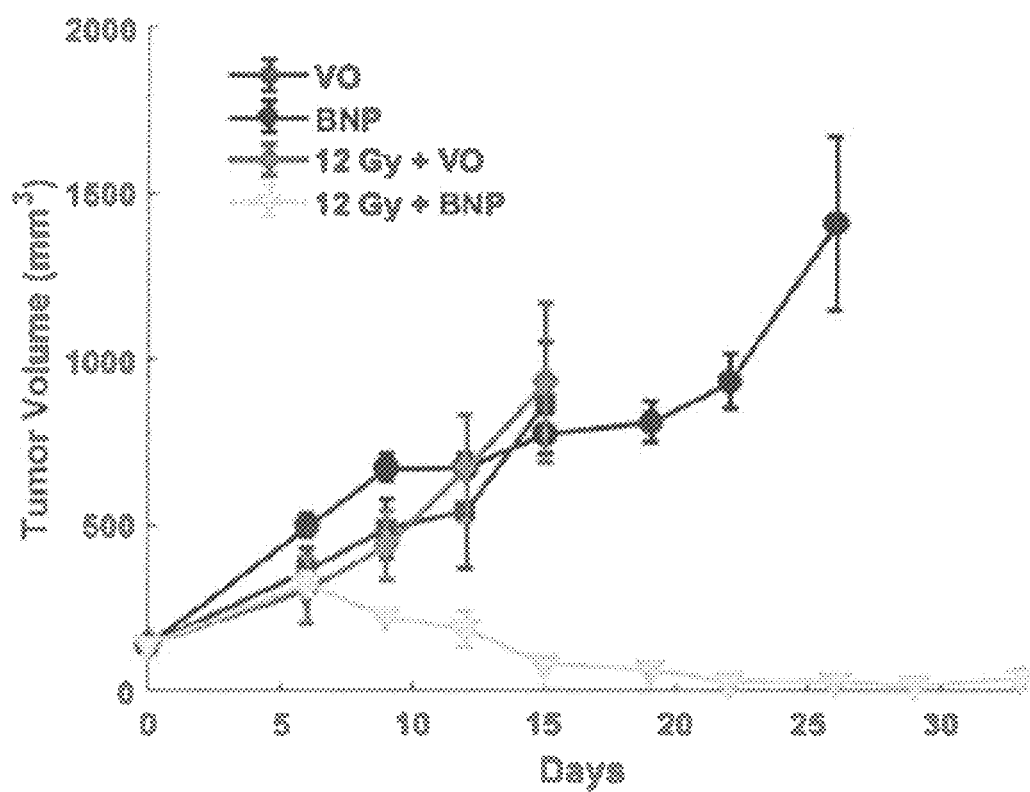
Figure 4B:
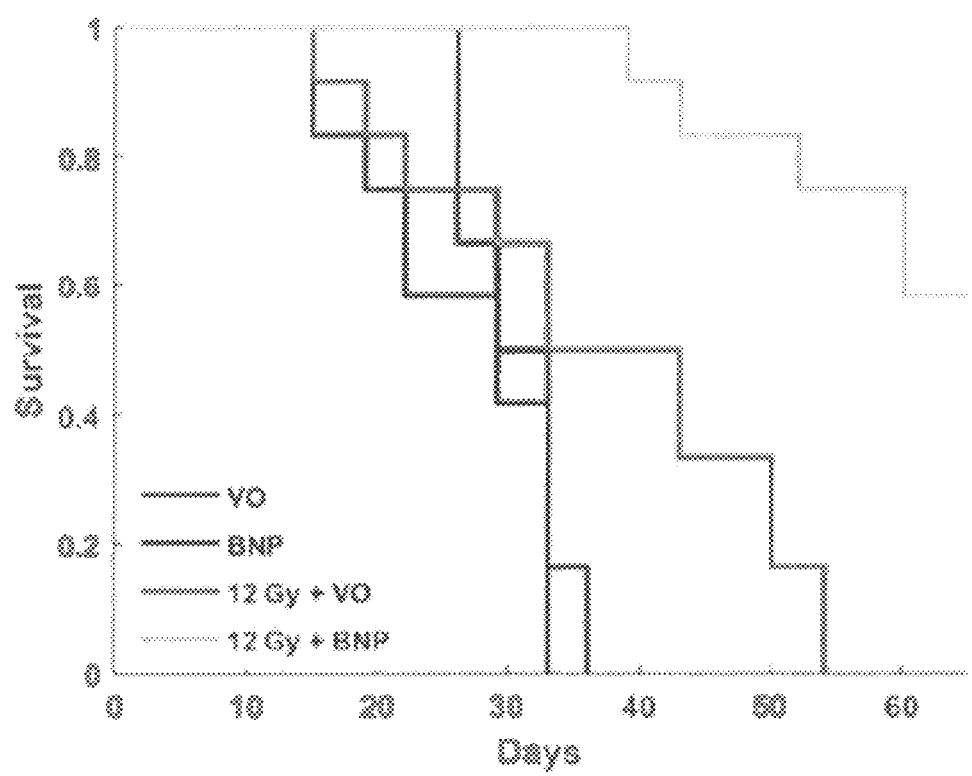
Figure 5:
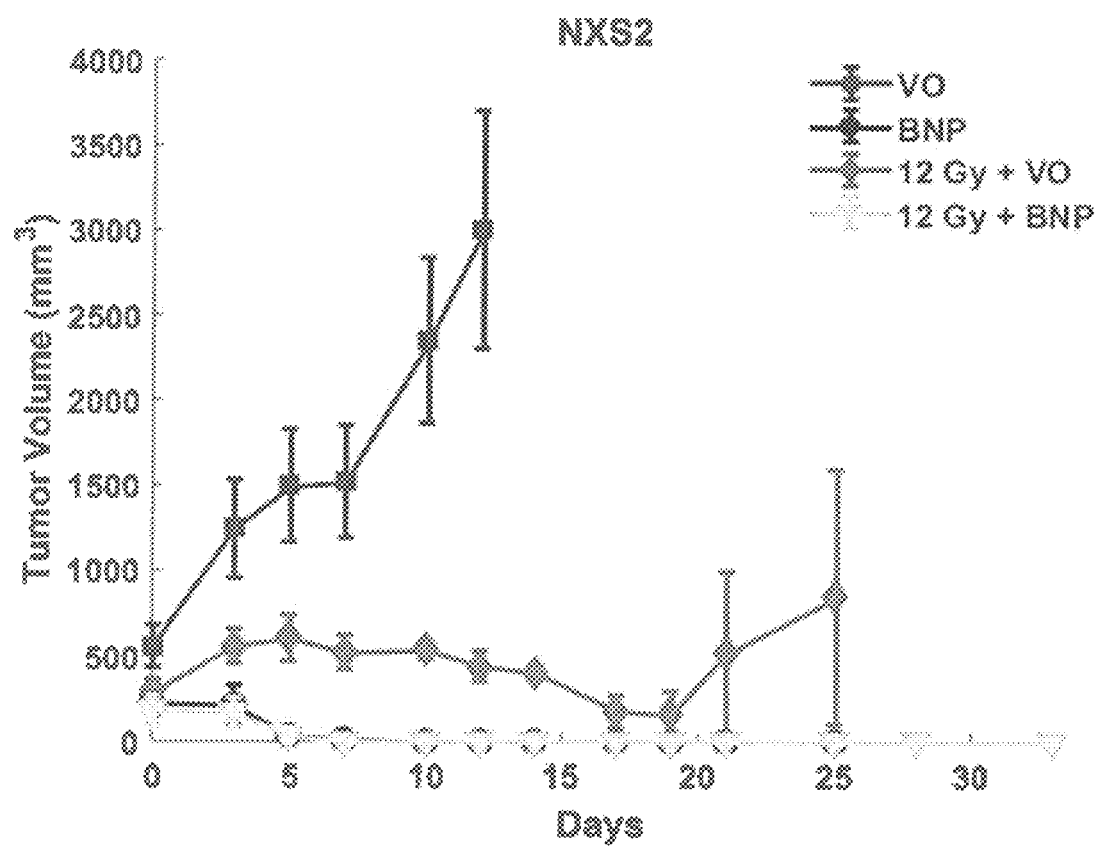
FIG. 5 Mean tumor volume curves comparing PBS control (i.e., VO), BNP alone, external beam radiation (EBRT) of 12 Gy alone, and BNP+12 Gy in an NXS2 neuroblastoma model.

Radiation, BNP, or combination treatment was compared to untreated controls in both B78 and NXS2 models. In the immunologically "cold" B78 tumor model, derived from B16 melanoma, BNP alone had no significant effect on tumor growth compared to PBS or RT alone; however, a 100% response rate was observed when combination RT+BNP was given (FIG. 4A-C). For NXS2 neuroblastoma, which is more immunogenic than B78 melanoma but functionally cold and not responsive to immune checkpoint inhibitors (ICIs), 87.5% (7/8) of the mice treated with BNP alone and 100% (8/8) of the mice treated with BNP+RT exhibited primary tumor complete regression (FIG. 5). A significant lower metastasis rate as well as improved survival were observed in these two groups of mice, compared to RT alone or PBS-control-treated mice. 37.5% (3/8) mice treated with BNP alone and 50% (4/8) mice treated with BNP+RT achieved CR, while all of the mice were dead within 45 days in the RT alone group. Death in mice with primary tumor CR appeared to be related to late metastatic relapse (data not shown). To test for immune memory, 90 days after initial treatment, mice with complete response (CR) were injected with the same cell line they had rejected.

Figure 6A:
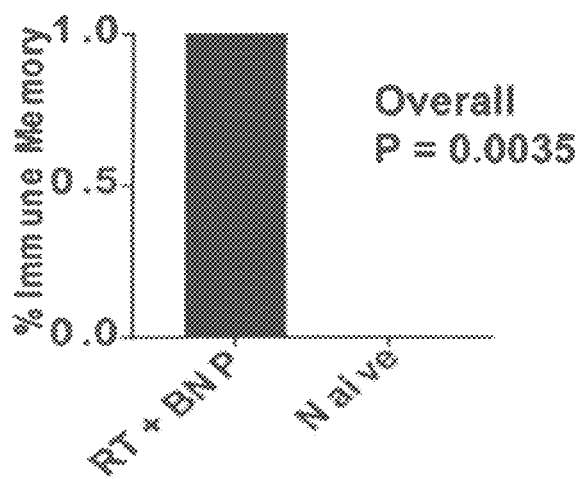
FIGS. 6A and 6B are graphs showing 90 days after treatment mice with complete response were injected with the same cell line they had rejected.
Figure 6B:
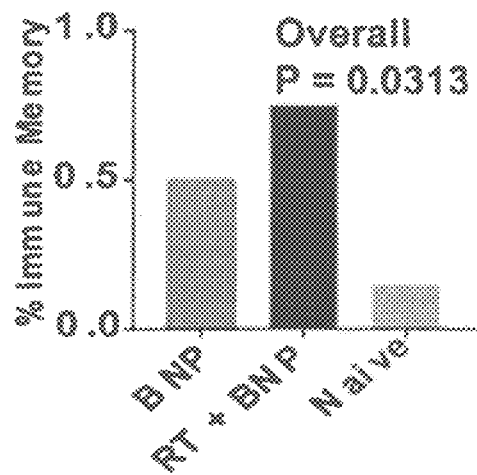

100% of the mice in the B78 group rejected tumor rechallenge, compared to 0% of the naïve control mice (FIG. 6A). This is consistent with the development of immunologic anti-tumor memory following RT+BNP. Among NXS2 mice with CR, those treated with RT+BNP exhibited a 75% rate of tumor rejection following rechallenge, compared to 50% among mice treated with BNP alone and 15% among naïve controls (FIG. 6B).

BNP Component Efficacy.

Figure 7:
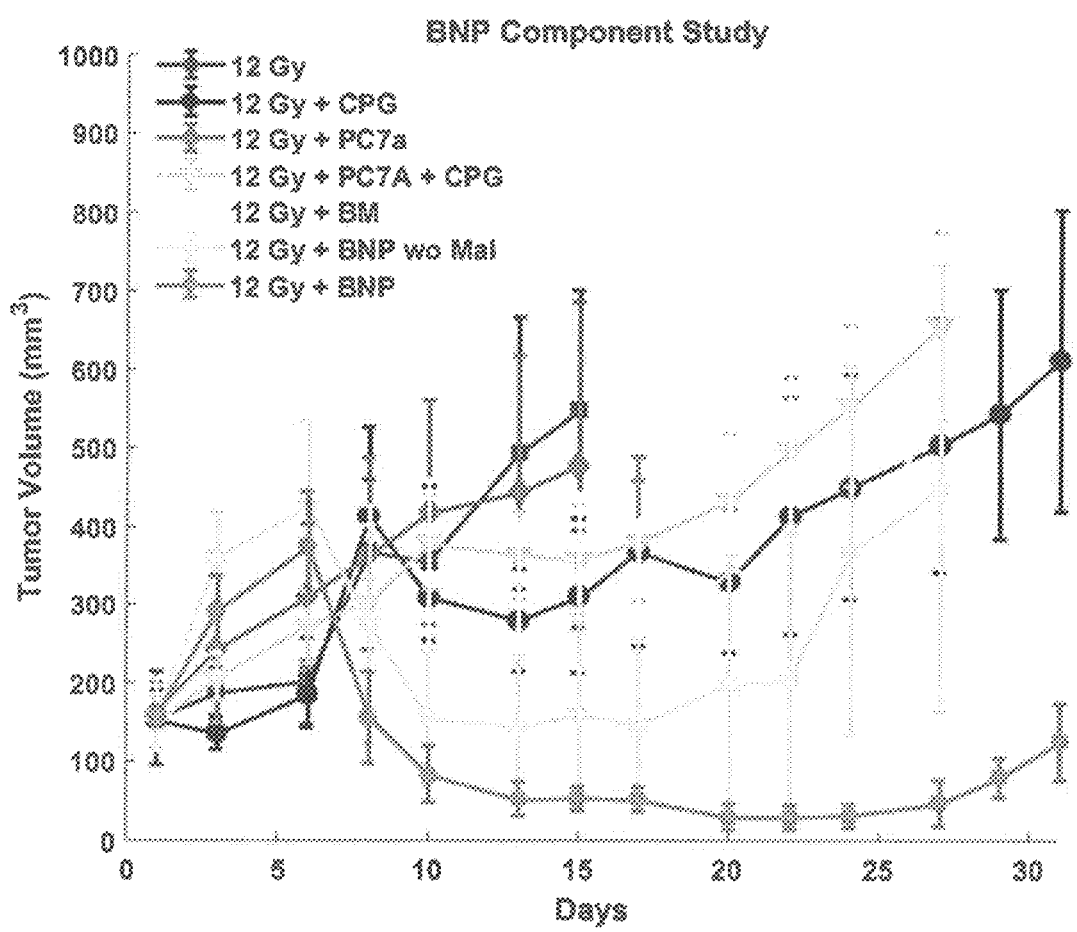
FIG. 7 Mean tumor volume curves comparing the response to 12 Gy EBRT alone vs 12 Gy EBRT with intratumoral injections of whole BNP or BNP component particles in a B78 melanoma model.

To test the efficacy of each component of our BNP, particles with different components were created including the full BNP, BNP without the maleimide group, the inner CpG-PC7A polyplex, CpG alone, PC7A alone, or bacterial membrane alone. BNP or BNP wo Mal significantly reduced tumor growth and increased mouse survival compared to all component groups, with the exception of RT+CpG (FIG. 7). RT+CpG also showed a trend towards improved anti-tumor response compared to RT alone. However, BNP did elicit significantly higher rates of CR when compared to RT+CpG: 55% vs 10% (p=0.018). The results demonstrate that the BNP designed to enhance tumor antigen cross presentation and anti-tumor immunity can improve the efficacy of RT in the treatment of immunologically "cold" tumor models.

CONCLUSIONS

The treatment combining BNP w/wo Mal and RT exhibited superior antitumor effectiveness compared to RT+BNP with lesser components. These findings suggest that efficient cancer immunotherapy is achieved when all factors involved including neoantigen exposure, uptake and presentation as well as immune cell maturation and activation are enhanced. In contrast to previous reports, the addition of Mal groups to the BNP had limited therapeutic effect. However, the examples demonstrate that this Mal group is functional and increases the uptake of tumor-specific antigen on the surface of the nanoparticle, which was taken up by and activates dendritic cells. Because tumor antigen uptake and cross-presentation by dendritic cells is such a critical step in the development of adaptive anti-tumor immunity, without wishing to be bound by theory it is speculated that this functional data provides rationale for inclusion of the Mal group in the BNP design.

In vivo treatment with RT+BNP resulted in increased levels of activated effector T cells, a Type I IFN response, a trend toward increased Mhc1 expression in the TME, marked tumor regression, improved overall survival, and potent anti-tumor immune memory in two distinct strains of mice bearing immunologically "cold" syngeneic tumors. This treatment modality has the potential to use patient's own neoantigens to achieve strong personalized immunotherapy by using off-the-shelf reagents. Additionally, combination RT+BNP treatment demonstrates the ability to deplete immunosuppressive Tregs and to recruit batF3 DCs to the TME which are essential for a long-term anti-tumor immune response. However, while this treatment has a very high response rate in both these tumor models as well as potential for long term cures with immune memory, resistance and late immune escape remain.

In monitoring mouse weight, posture, and behavior evidence of systemic toxicity or autoimmunity was not detected, however local inflammation and tumor ulceration was seen during treatment and resolved over time. Gene expression profiling of tumors treated with RT+BNP demonstrated activation of a type I IFN response, which should help initiate adaptive recognition of tumor cells. However, these studies also showed trends towards increased expression of immune suppressive genes, which may limit the response to RT+BNP and enable late tumor/metastatic progression. It is speculated these potential negative feedback mechanisms may be overcome by combining RT+BNP with ICIs that remove suppressive signaling, since early clinical data suggest that RT can increase the response rate to ICIs in some settings. The data suggests that RT+BNP can more effectively prime an adaptive immune response when compared to RT alone, which raises the possibility that RT+BNP may augment the depth of response to ICIs among patients with immunologically "hot" tumors, as well as the rate of response to ICI among patients with "cold" tumors.

REFERENCES

[1] S. Tsuji, M. Matsumoto, O. Takeuchi, S. Akira, I. Azuma, A. Hayashi, K. Toyoshima, T. Seya, *Infection and immunity* 2000, 68, 6883.

[2] E. Latz, A. Schoenemeyer, A. Visintin, K. A. Fitzgerald, B. G. Monks, C. F. Knetter, E. Lien, N. J. Nilsen, T. Espevik, D. T. Golenbock, *Nature inummunology* 2004, 5, 190.

[3] L. Cohn, L. Delamarre, *Front Immunol* 2014, 5.

[4] M. Luo, H. Wang, Z. Wang, H. Cai, Z. Lu, Y. Li, M. Du, G. Huang, C. Wang, X. Chen, M. R. Porembka, J. Lea, A. E. Frankel, Y.-X. Fu, Z. J. Chen, J. Gao, *Nat Nano* 2017, advance online publication.

[5] a) L. Müller, P. Aigner, D. Stoiber, *Front Immunol* 2017, 8, 304; b) S. Hadrup, M. Donia, P. thor Straten. *Cancer Microenvironment* 2013, 6, 123.

[6] S. Hamdy, A. Haddadi. R. W. Hung, A. Lavasanifar, *Adv Drug Deliver Rev* 2011, 63, 943.

[7] M. D. Garcia, R. Borrero, R. Marron, M. E. Lanio, L. Canet, O. Otero, R. Kadir, S. Suraiya, C. Zayas, Y. Lopez. M. N. Norazmi, M. E. Sarmiento. A. Acosta, *Bmc Immunol* 2013, 14.

[8] a) L. T. Nguyen Thi, R. Borrero Maura, S. Férnandez, G. Reyes, J. L. Perez, F. Reyes. M. d. I. A. Garefa, M. Fariñas, J. F. Infante, Y. Tirado, A. Puig, G. Sierra, N. Álvarez, J. C. Ramirez, M. E. Sarmiento, N. Mohd-Nor, A. Acosta, *Vaccimonitor* 2010, 19, 20; b) A. Adam, R. Ciorbazru, J. Petit. E. Lederer, in *Investigation and Stimulation of Immunity in Cancer Patients*, Springer, 1974. pp. 179.

[9] R. Bansal-Mutalik, H. Nikaido, *P Natl Acad Sci USA* 2014, 111, 4958.

[10] a) G. Zhu, G. M. Lynn, O. Jacobson. K. Chen, Y. Liu, H. Zhang, Y. Ma, F. Zhang, R. Tian, Q. Ni, *Nat Commun* 2017, 8, 1954; b) Yuanzeng Mini, 3, Kyle C. Roche1,2,3, Shaomin Tian2,4, Michael J. Eblan1,2,3, Karen P.McKinnon2,4, Joseph M. Caster1,2,3, Shengjie Chai2,5, Laura E. Herring6, Longzhen Zhang7, Tian Zhang8, Joseph M. DeSimone2,4,9,10,11,12. Joel E. Tepper1,2,3, Benjamin G. Vincent2,5, Jonathan S. Serody2,4,5 and Andrew Z. Wang1,2,3,7, *Nat Nanotechnol* 2017.

EQUIVALENTS

While certain embodiments have been illustrated and described, a person with ordinary skill in the art, after reading the foregoing specification, can effect changes, substitutions of equivalents and other types of alterations to the conjugates and nanoparticles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising." "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A nanoparticle comprising:
a polyplex core comprising one or more pH-responsive polymers and one or more anionic immune adjuvants; and
a shell of bacterial cell membrane components at least partially coating the polyplex core;
wherein:
each pH-responsive polymer comprises ionizable amine groups;
the one or more pH-responsive polymers are selected from the group consisting of polyacrylate esters, polymethacrylate esters, polyethyleneimines, polyalkyleneguanidines, cationic dendrimers, and cationic N-substituted poly(amino acids);
the bacterial cell membrane components are selected from Mycobacterium smegmatis or Mycobacterium bovis bacillus Calmette-Guerin (BCG) cell membrane components, and comprise a TLR 2 agonist, TLR 4 agonist, or a combination thereof; and
the shell of bacterial cell membrane components further comprises antigen capture groups exhibiting reactivity toward thiol and/or amino groups.

2. A nanoparticle comprising:
a polyplex core comprising one or more pH-responsive polymers and one or more anionic immune adjuvants; and
a shell of bacterial cell membrane components at least partially coating the polyplex core;
wherein:
each pH-responsive polymer comprises ionizable amine groups;
the one or more pH-responsive polymers are selected from the group consisting of polyacrylate esters, polymethacrylate esters, polyethyleneimines, polyalkyleneguanidines, cationic dendrimers, and cationic N-substituted poly(amino acids);
the bacterial cell membrane components are selected from Mycobacterium, Listeria or Escherichia coli cell membrane components, and comprise a TLR 2 agonist, TLR 4 agonist, or a combination thereof, and
the shell of bacterial cell membrane components further comprises antigen capture groups exhibiting reactivity toward thiol and/or amino groups.

3. A method of stimulating an immune response in a mammal comprising administering an effective amount of a nanoparticle of claim 1 to an irradiated tumor in the mammal, wherein the radiation was an amount effective to release cancer antigens from the tumor and stimulate the immune response.

4. A method of stimulating an immune response in a mammal comprising administering an effective amount of a nanoparticle of claim 2 to an irradiated tumor in the mammal, wherein the radiation was an amount effective to release cancer antigens from the tumor and stimulate the immune response.

5. The method of claim 3 wherein the nanoparticle is injected into the tumor and/or growth of the tumor is inhibited or the tumor shrinks.

6. The method of claim 4 wherein the nanoparticle is injected into the tumor and/or growth of the tumor is inhibited or the tumor shrinks.

7. The nanoparticle of claim 1, wherein the antigen capture groups exhibiting reactivity toward thiol and/or amino groups comprise maleimide, N-hydroxysuccinimide and/or 2-pyridinyldithio groups.

8. The nanoparticle of claim 1 wherein the ionizable amine groups are selected from amino, acyclic alkylamine, and/or cyclic amine.

9. The nanoparticle of claim 8 wherein the ionizable amine group is selected from $NH_2$, imidazolyl, pyrrolidinyl, piperidinyl and azepanyl.

10. The nanoparticle of claim 8 wherein the ionizable amine group is —NRR' wherein R and R' are independently selected from H, and $C_{1-4}$ alkyl.

11. The nanoparticle of claim 1 wherein the pH-responsive polymer is polymerized monomers of 2-(hexamethyleneimino) ethyl methacrylate (PC7A).

12. The nanoparticle of claim 1 wherein the anionic immune adjuvants are selected from the group consisting of CpG oligodeoxynucleotides, polyinosinic-polycytidylic acid, polyadenylic-polyuridylic acid, and polylactic-co-glycolic acid.

13. The nanoparticle of claim 1 wherein the weight ratio of pH responsive polymer to anionic adjuvant is about 1:1 to about 20:1.

14. The nanoparticle of claim 1 wherein the nanoparticle has a hydrodynamic diameter of about 100 to about 900 nm.

15. The nanoparticle of claim 1, wherein
the antigen capture groups exhibiting reactivity toward thiol and/or amino groups comprise maleimide, N-hydroxysuccinimide and/or 2-pyridinyldithio groups;
the ionizable amine group is selected from $NH_2$, imidazolyl, pyrrolidinyl, piperidinyl and azepanyl; and
the anionic immune adjuvants are selected from the group consisting of CpG oligodeoxynucleotides, polyinosinic-polycytidylic acid, polyadenylic-polyuridylic acid, and polylactic-co-glycolic acid.

16. The nanoparticle of claim 15, wherein the pH-responsive polymer is polymerized monomers of 2-(hexamethyleneimino) ethyl methacrylate (PC7A).

17. The nanoparticle of claim 16, wherein the weight ratio of pH responsive polymer to anionic adjuvant is about 1:1 to about 20:1.

18. The nanoparticle of claim 2, wherein the antigen capture groups exhibiting reactivity toward thiol and/or amino groups comprise maleimide, N-hydroxysuccinimide and/or 2-pyridinyldithio groups.

19. The nanoparticle of claim 2 wherein the ionizable amine groups are selected from amino, acyclic alkylamine, and/or cyclic amine.

20. The nanoparticle of claim 2 wherein the pH-responsive polymer is polymerized monomers of 2-(hexamethyleneimino) ethyl methacrylate (PC7A).

21. The nanoparticle of claim 2 wherein the anionic immune adjuvants are selected from the group consisting of CpG oligodeoxynucleotides, polyinosinic-polycytidylic acid, polyadenylic-polyuridylic acid, and polylactic-co-glycolic acid.

22. The nanoparticle of claim 2 wherein the weight ratio of pH responsive polymer to anionic adjuvant is about 1:1 to about 20:1.

23. The nanoparticle of claim 2, wherein
the antigen capture groups exhibiting reactivity toward thiol and/or amino groups comprise maleimide, N-hydroxysuccinimide and/or 2-pyridinyldithio groups;
the ionizable amine group is selected from $NH_2$, imidazolyl, pyrrolidinyl, piperidinyl and azepanyl; and
the pH-responsive polymer is polymerized monomers of 2-(hexamethyleneimino) ethyl methacrylate (PC7A).

* * * * *